United States Patent [19]

Ryschka et al.

[11] Patent Number: 4,625,779

[45] Date of Patent: Dec. 2, 1986

[54] RECEIVING ARRANGEMENT FOR FILLING AN ANAESTHETIC FLUID

[75] Inventors: Martin Ryschka, Stockelsdorf; Helmut Mohr, Lübeck; Wolfgang Falb, Krummesse; Carl-Friedrich Wallroth, Lübeck, all of Fed. Rep. of Germany

[73] Assignee: Drägerwerk Aktiengesellschaft, Lübeck, Fed. Rep. of Germany

[21] Appl. No.: 779,384

[22] Filed: Sep. 23, 1985

[30] Foreign Application Priority Data

Sep. 22, 1984 [DE] Fed. Rep. of Germany ....... 3434966

[51] Int. Cl.⁴ .............................................. B65B 3/04
[52] U.S. Cl. ................................. 141/311 R; 141/350
[58] Field of Search ...................... 141/311 R, 348-362

[56] References Cited

U.S. PATENT DOCUMENTS 3,875,980  4/1975  Getz ..................................... 141/311

Primary Examiner—Houston S. Bell, Jr.
Attorney, Agent, or Firm—Walter Ottesen

[57] ABSTRACT

A receiving arrangement is disclosed for filling an anaesthetic medium from a supply vessel into the charging chamber of an anaesthetic apparatus. The supply vessel is connectable to the arrangement by means of a coupling piece. The arrangement includes a receiving structure having an input opening for receiving the coupling piece therein and a connecting part disposed adjacent the receiving structure. The connecting part includes channels communicating with the charging chamber for conducting the anaesthetic medium to the latter. A closure piece is slidably mounted in the receiving structure to slide between a first position opposite the ports and a second position whereat the closure piece is displaced away from the ports. A resilient biasing spring biases the closure piece into the first position. A drive moves the receiving structure between a rest location whereat the closure piece seals the ports with respect to the ambient and an actuating location whereat the receiving structure and the closure piece are displaced away from the ports. The receiving structure can now receive the coupling piece thereby causing the closure piece to be displaced to its second position. The coupling piece and the connecting part conjointly define a connecting interface whereat the anaesthetic medium flows from the coupling piece into the channels when the structure is returned to the rest location with the coupling piece inserted therein. A blocking piece blocks the entry of the coupling piece through the opening when the receiving structure is in its rest location.

9 Claims, 4 Drawing Figures

RECEIVING ARRANGEMENT FOR FILLING AN ANAESTHETIC FLUID

FIELD OF THE INVENTION

The invention relates to a receiving arrangement for filling an anaesthetic fluid into the charging chamber of an anaesthetic apparatus from a supply vessel. The supply vessel is connectable to the receiving arrangement by means of a coupling piece. The receiving arrangement has an input opening for the coupling piece and a closure piece and, in the rest position, the ports of the channels necessary for filling are closed by means of the closure piece.

BACKGROUND OF THE INVENTION

German Pat. No. 19 00 271 discloses such an arrangement for filling an anaesthetic liquid from a bottle in the charging chamber of an anaesthetic apparatus. The arrangement includes a coupling piece, a liquid charging conduit and a ventilating conduit which terminate with their ports in a connecting channel which is connected to the charging chamber. During the filling operation, the coupling piece lies seal-tight against the connecting channel with both of its air and liquid conduits. When the filling of the charging chamber is completed, the input opening must be closed in a seal-tight manner with a separate closure piece.

The publication entitled "Safety Filling System for Vapor 19.1", Drägerwerk Aktiengesellschaft, 2nd edition, February 1983, discloses a further arrangement for filling an anaesthetic liquid into the charging chamber of an anaesthetic apparatus which has a receiving member wherein a coupling piece is introduced having two openings for the liquid channel and the air channel for filling the charging chamber. Both openings of the channel are pressed against the corresponding openings in the housing of the apparatus by means of a pressure screw, the openings being provided with a sealing ring. After the filling operation is ended, the pressure screw must be completely released before the coupling piece can again be withdrawn from the receiving member. Thereafter, the opening in the housing must be closed again by means of a closure piece which must be pressed in a seal-tight manner against the openings leading to the filling chamber and located in the housing by means of the pressure screw.

The filling procedure with the aid of the known apparatus requires several manual steps sequentially arranged one with respect to the other which must be carried out carefully and conscientiously by the person conducting the filling operation. It is especially necessary that the coupling piece and the closure piece be tightly closed by means of the pressure screw so that leaks during filling or the run-out of anaesthetic vapors are prevented during an anaesthetic ventilation. The pressure screw must be completely released when introducing the coupling piece and closure piece in order to provide sufficient free space for introducing the coupling piece and closure piece. If this is not the case, the danger exists that the seals with which the connecting openings for the connecting channels are supplied will be damaged or the coupling piece can not be introduced up to the stop so that the openings in the coupling piece do not overlap with those in the housing whereby a filling becomes impossible.

SUMMARY OF THE INVENTION

It is an object of the invention to improve an arrangement of the kind referred to above so that the introduction of the coupling piece can only occur if the input opening is completely free and so that the rest position is first then taken up when the coupling piece with its required length is completely inserted into the input opening of the receiving arrangement.

According to a feature of the invention, the receiving arrangement includes a receiving member wherein the closure piece is slidably mounted against a return force. The receiving member is moved out of its rest position, whereat a stop blocks the input opening, into an actuating position whereat the closure piece or coupling piece is spaced from the ports in the connecting region and the input opening is clear of the stop.

Such a filling arrangement has a rest position wherein the closure piece continuously lies against the ports of the filling channels in a seal-tight manner. A displacement of the closure piece by means of the coupling piece can only occur if the input opening is completely cleared by actuating the drive so that the coupling piece for filling the charging chamber can first then be introduced when the sealing surfaces at the ports of the channels are free. With the coupling piece introduced, the arrangement is then first moved out of the actuating position into the rest position when the coupling piece is introduced so far that the stop fixes the coupling piece to prevent a displacement of the coupling piece during the filling operation.

The closure piece can be pushed by means of a resilient member, preferably a helical spring, within the receiving member when the coupling piece is withdrawn after a completed filling operation so that the closure piece closes the ports of the channels in a seal-tight manner in the rest position.

According to another embodiment of the invention and after a completed insertion of the coupling piece, the closure piece actuates a switching unit for initiating a suction action by means of which possible leakages of anaesthetic gas during the actuated position are removed. In the actuated position, the ports of the channels and the openings of the coupling piece are exposed.

Several channels are advantageously provided for filling the charging chamber. Of these channels, one is the input channel, a second channel is the ventilating channel and a third channel is the overflow channel. All channels project to different depths of penetration into the charging chamber in correspondence with their function. In this connection, the ventilating channel includes a check-valve by means of which a flooding of the ventilating channel is prevented when the supply vessel is lifted.

The closure piece includes an opening which is arranged to be opposite the port of the overflow channel when the coupling piece is completely inserted, so that in the event of a failure, an exiting of excess anaesthetic fluid is possible.

The changeover between rest position and actuating position of the receiving arrangement occurs by means of a stroke-drive which can be actuated by means of a manipulator which can be either mounted directly on the drive or can be connected with the drive via a connecting conduit for remote actuation. Known arrangements can be utilized as the drive. Such arrangements can comprise hydraulically actuated members which are suitable to transfer a stroke movement by means of a transfer member to the receiving member.

BRIEF DESCRIPTION OF THE DRAWING

The invention will now be described with reference to the drawing wherein.

DESCRIPTION OF THE PREFERRED EMBODIMENTS OF THE INVENTION

Figure 2:
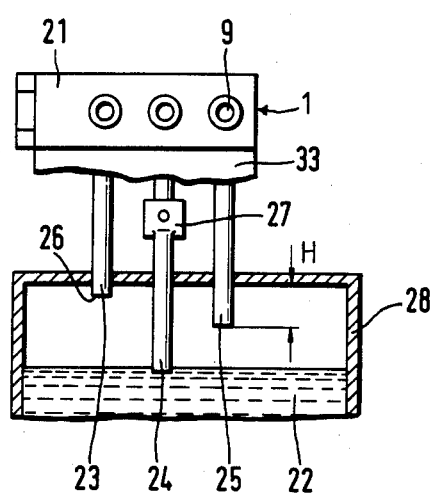
FIG. 2 is a view taken along line 2—2 through the filling chamber with the connecting part for the filling channels.
Figure 1:
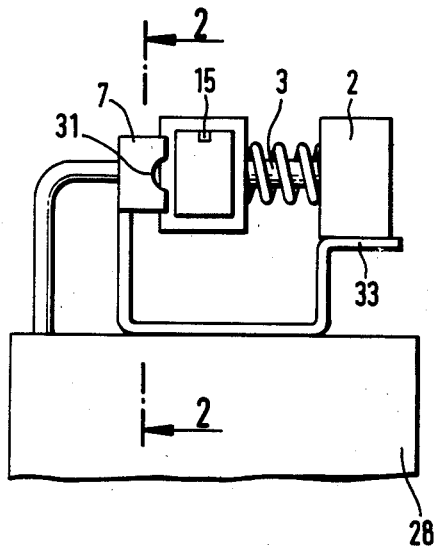
FIG. 1 is a front elevation view of a receiving arrangement according to the invention in the actuated position.
Figure 3:
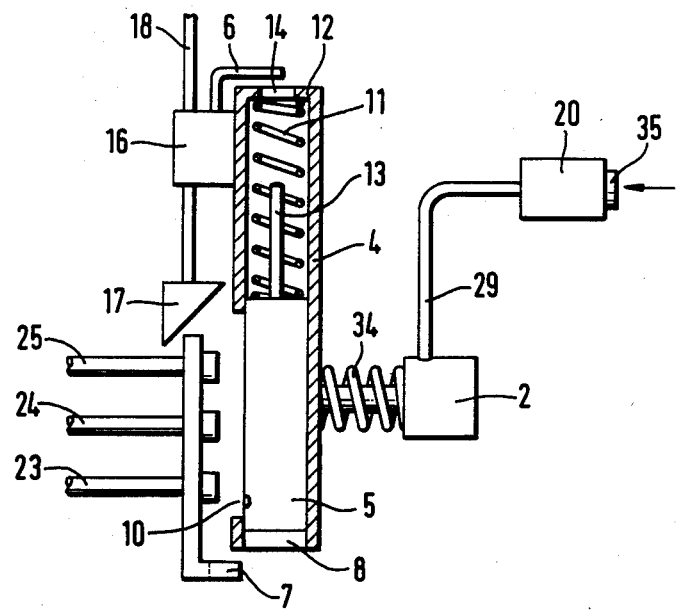
FIG. 3 is a plan view, partially in section, of the receiving arrangement again in the actuated position; and, FIG. 4 is a further plan view, partially in section, of the receiving arrangement for filling an anaesthetic liquid.
Figure 4:
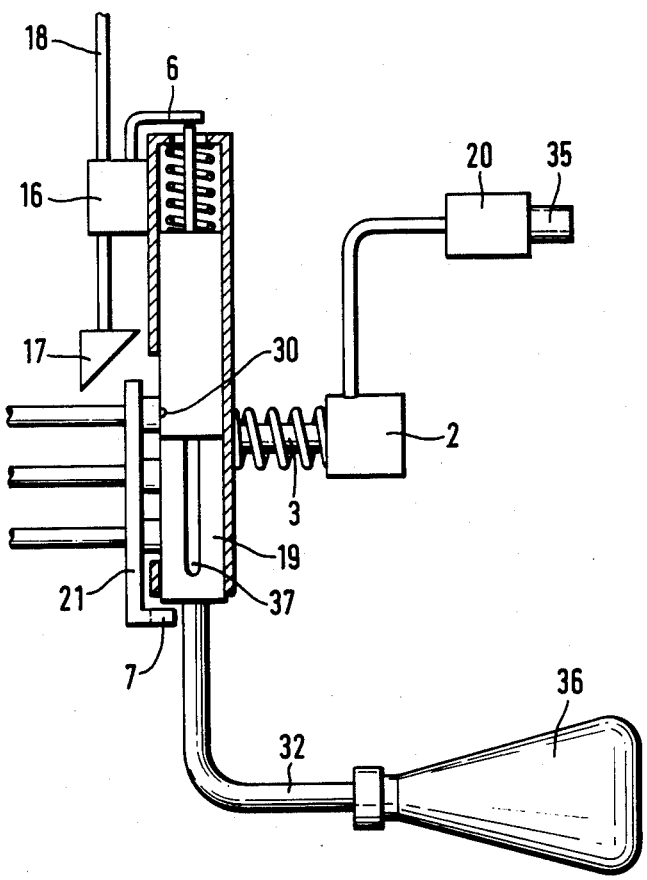

The receiving arrangement is attached to the upper end of a charging chamber 28. This charging chamber 28 can be a tank which is connected via a metering pump with an anaesthetic apparatus.

However, the tank can also be a chamber of a vaporizer which is switched into the fresh gas stream of an anaesthetic apparatus. In lieu of a mounting on a cover as shown, it is understood that a lateral mounting or a mounting in any other favorable position is possible.

The receiving arrangement 1 includes a connecting member 21 which continues into a carrier 33 for mounting the receiving arrangement 1. In the connecting member 21, a filling channel 23, a ventilating channel 24 and an overflow channel 25 all terminate one next to the other in corresponding ports 9. The channels 23 to 25 project into the interior of the filling chamber 28 to respectively different depths H. An end face of the connecting member 21 defines a stop 7 which has a recess 31.

A hydraulic drive 2 is mounted on an offset end of the carrier 33. A manipulator 20 is connected with the hydraulic drive 2 via a remote actuating conduit 29. The manipulator 20 permits a shortening of the outer length of the transmitting member 3 against the force of a pressure spring 34 when the push button 35 is pressed. The previous condition is again established by the pressure spring 34 when the push button 35 is released. The outer end of the transfer member 3 is connected to receiving member 4 which is pressed by pressure spring 34 in the direction toward the connecting member 21 and is displaceable away from the ports 9 by means of the drive 2.

The receiving member 4 has a hollow space of cornered cross section and has an input opening 8 at the end thereof facing the stop 7 as well as a wall portion 12 at the opposite end. A code pin 15 prpjects from above into the input opening 8 and simultaneously forms the abutment for a closure piece 5 which is displaceably mounted in receiving member 4 against the force of spring 11. The receiving member 4 includes a broken-out connecting region 10 opposite the connecting member 21 in the region of ports 9 so that the closure piece 5 can lie seal-tight against the ports 9 under the force of spring 34. In this position of the receiving member 4 the stop 7 overlaps a portion of the input opening 8.

The closure piece 5 carries an actuating piece 13 which penetrates outwardly through an opening 14 in the wall portion 12 and can actuate lever 6 of a suction valve 16. The suction valve 16 connects a hood 17 mounted in the region of the connecting member 21 with a suction conduit 18.

In the rest position of the receiving member 4, the closure piece 5 lies against the ports 9 and closes the same in a seal-tight manner. To start the filling procedure, the closure piece 5 is lifted from the ports 9 via the receiving member 4 by applying pressure to the push button 35. Simultaneously, the input opening 8 moves entirely from beneath the stop 7. Now the coupling piece 19 can be introduced into the input opening 8. The coupling piece 19 is connected with the supply vessel 36 for the anaesthetic medium via the flexible filling hose 32. At the same time, a coded slot 37 receives the code pin 15. In this way, the closing piece 5 is pushed back and its actuating piece 13 actuates the lever 6 of the suction valve 16 and switches on the suction for the hood 17. The coupling piece 19 has two openings corresponding to the ports 9 of the filling channel 23 and the ventilating channel 24. After releasing the push button 35, the coupling piece 19 is pressed against the ports 9 in a seal-tight manner by means of the pressure spring 34. At the same time, the stop 7 engages the rearward end of the coupling piece 19 and prevents an unwanted slipping out of the input opening 8.

The flexible filling hose 32 comprises two concentric conduits. The interior of the upwardly lifted supply vessel 36 is now connected with the interior of the filling chamber 28 via the filling hose 32 and the anaesthetic liquid flows via the filling channel 23 into the filling chamber 28 while the gaseous content flows back into the supply vessel 36 via the ventilating channel 24 to compensate. A check-valve 27 prevents flooding of the ventilating conduit when the filling process is started.

As soon as the level of liquid reaches the opening of the ventilating channel 24, no more gas can flow back into the supply vessel 36 and therefore no anaesthetic fluid can exit from the vessel and the filling process is ended.

In the event of a failure such as because of a threaded fastening which is not tight, a penetration of air into anaesthetic vessel 36 is then nevertheless possible, the anaesthetic fluid 22 which then continues to flow exits to the ambient after reaching opening 26 of the overflow channel 25 via an opening 30 in the closing piece 5 and indicates a failure. After completing the filling process, the supply vessel 36 is lowered and the coupling piece 19 is released from the ports 9 by means of a renewed pressure on the push button 35 and is pushed out from the closing piece 5 under the pressure of spring 11. After the push button 35 is released, the closing piece 5 closes the openings 9.

It is understood that the foregoing description is that of the preferred embodiments of the invention and that various changes and modifications may be made thereto without departing from the spirit and scope of the invention as defined in the appended claims.

What is claimed is:

1. A receiving arrangement for filling an anaesthetic medium from a supply vessel into the charging chamber of an anaesthetic apparatus, the supply vessel being connectable to the arrangement by means of a coupling piece, the arrangement comprising:
   a receiving structure having an input opening for receiving said coupling piece therein;
   a connecting part disposed adjacent said receiving structure and including channel means communicating with said charging chamber for conducting the anaesthetic medium to the latter, said channel means terminating in port means facing said receiving structure;

said receiving structure further including a closure piece slidably mounted in said structure between a first position directly opposite said port means and a second position whereat said closure piece is displaced away from said port means thereby making the latter accessible to said coupling piece after the latter is inserted into said receiving structure through said opening; and, resilient biasing means for biasing said closure piece into said first position;

drive means for driving said receiving structure between a rest location whereat said closure piece seals said port means with respect to the ambient when in said first position to an actuating location whereat said receiving structure and said closure piece are displaced away from said port means and whereat said receiving structure can receive said coupling piece therein so as to cause said closure piece to be displaced to said second position against the force of said resilient biasing means so that said coupling piece occupies said first position;

said coupling piece and said connecting part conjointly defining a connecting interface whereat said anaesthetic medium flows from said coupling piece into said port means when said structure is returned to said rest location with said coupling piece inserted therein; and, blocking means for blocking the entry of said coupling piece through said opening when said receiving structure is in said rest location and for blocking an unwanted slippage of said coupling piece out of said opening when said structure is at said rest location with said coupling piece inserted therein.

2. The receiving arrangement of claim 1, said receiving structure being a hollow elongated structure having said inlet opening at one longitudinal end thereof, said elongated structure having an end wall defining the other longitudinal end thereof; said closure piece being slidably mounted within said structure, said resilient biasing means being a spring member disposed between said end wall and said closure piece.

3. The receiving arrangement of claim 2, said spring member being a helical spring.

4. The receiving arrangement of claim 1, comprising suction means for drawing away any leaked quantities of said anaesthetic medium at said connecting interface.

5. The arrangement of claim 4, said suction means comprising switch means operatively connected to said closure piece for initiating the suction action when said closure piece is moved into said second position.

6. The receiving arrangement of claim 1, comprising code means formed on said structure at said opening and on said coupling piece for ensuring that only predetermined coupling pieces can be inserted into said input opening whereby only storage vessels containing the desired anaesthetic medium can be emptied into said charging chamber.

7. The receiving arrangement of claim 1, said connecting part further including an overflow channel communicating with said charging chamber, said overflow channel terminating in an overflow port facing said receiving structure; said first-mentioned channel means comprising a filling channel and a ventilating channel, said three channels extending into said charging chamber at respectively different depths, said connecting part further including a check valve mounted in said ventilating channel.

8. The receiving arrangement of claim 7, said closure piece having a recess formed therein open to the ambient, said recess being located on said closure piece so as to coact with said overflow port when said closure piece is in said second position.

9. The arrangement of claim 1, said drive means comprising: a displacement drive device for displacing said receiving structure through a predetermined stroke movement; and, manipulator means for actuating said drive device.

* * * * *